United States Patent [19]
Harklau et al.

[11] Patent Number: 5,574,288
[45] Date of Patent: Nov. 12, 1996

[54] METHOD FOR MEASURING RESIDUAL RADIATION-CURABLE MONOMERS OR OLIGOMERS

[75] Inventors: Lanny L. Harklau, Stillwater; J. Thomas Simpson, Lake Elmo, both of Minn.

[73] Assignee: Minnesota Mining and Manufacturing Company, St. Paul, Minn.

[21] Appl. No.: 423,204

[22] Filed: Apr. 17, 1995

[51] Int. Cl.$^6$ .................................................. G01N 21/64
[52] U.S. Cl. ..................................... 250/459.1; 250/461.1
[58] Field of Search ............................ 250/459.1, 461.1, 250/458.1; 356/417; 436/172

[56] References Cited

U.S. PATENT DOCUMENTS

| | | | |
|---|---|---|---|
| 4,391,687 | 7/1983 | Vesley | 204/159.16 |
| 4,561,011 | 3/1987 | Ors et al. | 250/459.1 |
| 4,922,113 | 5/1990 | Melancon | 250/372 |
| 4,978,731 | 12/1990 | Melancon et al. | 528/15 |
| 5,037,763 | 8/1991 | Petisce | 436/172 |
| 5,047,444 | 9/1991 | DeVoe et al. | 522/99 |
| 5,087,670 | 2/1992 | Melancon et al. | 525/326.2 |
| 5,100,802 | 3/1992 | Mickols | 436/34 |
| 5,128,102 | 7/1992 | Kaneko et al. | 250/459.1 |
| 5,270,116 | 12/1993 | Melancon et al. | 428/447 |
| 5,302,627 | 4/1994 | Field et al. | 522/13 |
| 5,310,604 | 5/1994 | Melancon et al. | 428/447 |
| 5,341,676 | 8/1994 | Gouterman et al. | 250/459.1 |

OTHER PUBLICATIONS

Bulletin of the Chemical Society of Japan, "Studies on s-Triazines. I. Cotrimerization of Trichloroacetonitrile with Other Nitriles", vol. 42, pp. 2924–2930 (1969).

*Primary Examiner*—Davis L. Willis
*Assistant Examiner*—Richard Hanig

[57] ABSTRACT

A method of measuring intensity of radiant energy fluoresced by a fluorescer in a radiation-cured coating. The method comprising the steps of: a) providing a coating comprising: i) a radiation-curable monomer or oligomer; and ii) a fluorescer having an excitation energy at a wavelength $\lambda_2$, the fluorescer fluorescing radiant energy of a wavelength $\lambda_3$; b) curing the coating by exposure to radiant energy, thereby changing the intensity of radiant energy that would be fluoresced by the fluorescer if exposed to wavelength $\lambda_2$; c) illuminating the radiation-cured coating with excitation energy of a wavelength $\lambda_2$, wherein at least 50% of the excitation energy is absorbed by the upper 75 μm of the radiation-cured coating; and d) measuring the intensity of the radiant energy fluoresced by the fluorescer at wavelength $\lambda_3$. The above method can be used to measure the amount of residual radiation-curable monomer or oligomer present in a radiation-cured coating. This method of measuring residual monomer is especially useful where the intensity of the radiant energy fluoresced by the fluorescer at wavelength $\lambda_3$ changes with the concentration of unreacted radiation-curable monomer or oligomer in the radiation-cured coating.

27 Claims, 5 Drawing Sheets

METHOD FOR MEASURING RESIDUAL RADIATION-CURABLE MONOMERS OR OLIGOMERS

FIELD OF THE INVENTION

This invention relates to a method of measuring fluorescence in order to determine the level of cure of a radiation-cured material. More particularly, this invention relates to a method of measuring the amount of residual radiation-curable monomer or oligomer present in a radiation-cured material.

BACKGROUND OF THE INVENTION

Radiation-cured materials, e.g., radiation-cured coatings, exist throughout industry. Radiation-cured coatings are used in the manufacture of floor tiles, furniture, medical syringes, compact discs, computer floppy disks, video and audio tapes and glass fiber composites for automobiles and other products.

In the production of radiation-cured coatings, it is desirable to determine the coating's level of cure, i.e., the degree to which the original radiation-curable monomers or oligomers have been reacted to form a cured product. Improperly cured coatings can exhibit generally poor quality characteristics relative to properly cured coatings, for example, poor adhesion to a substrate, poor abrasion resistance, etc. Coatings cured on a release liner, if over-cured or under-cured will display inconsistent release properties. And, the unreacted or "residual" monomers of an improperly cured coating can cause an unpleasant odor. Proper curing eliminates many of these problems, and provides consistent quality of cured products.

A cured material's general extent of cure can be determined by several methods. Some methods correlate a physical property of the cured coating, e.g., modulus, with a known level of cure. Testing that physical property gives an indirect measure of a material's level of cure. These "bulk" methods are limited to measuring physical properties, and therefore are not a direct determination of the residual monomer content of a cured coating. Further, these bulk methods must generally be performed "off-line."

To test a sample off line, a production line must be shut down for the time necessary to perform the desired test. In some cases, this can require several hours. Such a shutdown causes waste, lost productivity, and importantly, prevents the test data from being used to optimize run conditions because the production line must be re-started.

To measure the general extent of cure on-line, fluorescent additives have been included in radiation-cured coatings. As a radiation-cured material cures, its viscosity increases. The intensity of fluorescence from a fluorescent additive can be dependent upon the material's viscosity and therefore on its level of cure. A problem with this type of cure measurement system is that fluorescers are generally insensitive to changes above a certain viscosity. Therefore, these systems cannot distinguish differences in levels of cure at higher conversions, or small changes in residual monomer concentration.

A method of more directly measuring the residual monomer content of a cured material is known as "redry." Redry measures the change in mass of a sample due to evaporation of residual monomers. Redry measurements, however, like the bulk tests, can only be performed off line.

What is needed, but what is not provided by the prior art, is a system to measure with precision the residual monomer content of a radiation-cured coating, especially in a system that has been cured to high conversions, e.g., less than 10% residual monomer or oligomer remaining in the radiation-cured coating. Preferably, the method should allow the measurement of residual monomer content in real time, and on-line.

SUMMARY OF THE INVENTION

The present invention relates to a method of determining the extent of cure of a radiation-cured material by determining the amount of residual radiation-curable monomer or oligomer present in that material. The method is far more sensitive than other methods of measuring cure, and can detect very small differences in the residual monomer concentration of radiation-cured coatings. Further, the method can measure the amount of residual radiation-curable monomer or oligomer present at the surface, or within an upper portion of a radiation-cured coating. The method can be used to design and control curing processes. Preferably, the method can be performed in real time to monitor residual monomer content of a radiation-cured coating on-line, as the coating is being manufactured.

An aspect of the present invention is a method of measuring intensity of radiant energy fluoresced by a fluorescer in a radiation-cured coating. The method comprises the steps of: a) providing a coating comprising: i) a radiation-curable monomer or oligomer; and ii) a fluorescer having an excitation energy at a wavelength $\lambda_2$, the fluorescer fluorescing radiant energy of a wavelength $\lambda_3$; b) curing the coating by exposure to radiant energy, thereby changing the intensity of radiant energy that would be fluoresced by the fluorescer if exposed to wavelength $\lambda_2$; c) illuminating the radiation-cured coating with excitation energy of a wavelength $\lambda_2$, wherein at least 50% of the excitation energy is absorbed by the upper 75 µm of the radiation-cured coating; and d) measuring the intensity of the radiant energy fluoresced by the fluorescer at wavelength $\lambda_3$.

Another aspect of the present invention relates to using the above method of measuring fluorescence emission intensity to measure the amount of residual radiation-curable monomer or oligomer present in a radiation-cured coating. This method of measuring residual monomer or oligomer is especially useful where the intensity of the radiant energy fluoresced by the fluorescer at wavelength $\lambda_3$ changes with the concentration of unreacted radiation-curable monomer or oligomer in the coating.

The fluorescence emission intensity measurement of the present invention also leads to other valuable information. For instance, the curing reactions of some radiation-cured coatings are inhibited by oxygen. These coatings are often cured in an atmosphere of inert gas, e.g., a curing chamber purged with nitrogen gas. To provide optimum cure conditions, the present invention allows measurement of the amount of oxygen present in a purged cure chamber.

Where oxygen acts to inhibit a cure reaction, individual oxygen-sensing "probes" have in the past been used at various locations inside of a cure chamber to detect oxygen. These probes are able to detect the presence of oxygen in the bulk atmosphere contained in the cure chamber. These probes, however, are incapable of measuring the amount of oxygen present at the coating surface because such probes cannot be placed in close proximity to the coating surface being cured. The present invention overcomes the limitations inherent in the use of oxygen sensing probes.

A further aspect of the present invention is a method of measuring the concentration of oxygen in a cure chamber. The method comprises the steps of: a) providing a coating in a cure chamber, the coating comprising: i) a radiation-curable monomer or oligomer; and ii) a fluorescer having an excitation energy at a wavelength $\lambda_2$, the fluorescer fluorescing radiant energy of a wavelength $\lambda_3$, wherein the intensity of the fluoresced radiant energy at wavelength $\lambda_3$ changes with the concentration of oxygen in the cure chamber at the time the coating is cured; b) curing the coating by exposure to radiant energy; c) illuminating the radiation-cured coating with excitation energy of a wavelength $\lambda_2$; d) measuring the intensity of the radiant energy fluoresced by the fluorescer at wavelength $\lambda_3$; and e) relating the intensity of the radiant energy fluoresced by the fluorescer at $\lambda_3$ to the concentration of oxygen present in the cure chamber at the time the coating is cured by reference to predetermined calibration data.

As used herein:

"90% cure" refers to a radiation-cured coating that contains 10% by weight of radiation curable monomer or oligomer;

"Curing" refers to a reaction which polymerizes or copolymerizes radiation-curable monomers or oligomers at least to a degree to cause an increase in the viscosity of a radiation-curable composition;

A "radiation-cured" material is a material, for example a coated material or coating, comprising radiation-curable monomers or oligomers, that has been exposed to radiant energy causing the radiation-curable monomers or oligomers to be polymerized or copolymerized at least to a degree to cause an increase in the viscosity of the material;

A "spectroscoptically detectable amount" of radiation is an amount that can be observed in a conventional (commercially available) spectroscope.

BRIEF DESCRIPTION OF THE DRAWINGS

FIG. 2 shows the absorbance behavior before cure, and after cure by exposure to 500 mj/cm² of 360 nm light. FIG. 2 also shows the absorbance of the BOPP substrate.

DESCRIPTION OF THE PREFERRED EMBODIMENTS

Figure 1:
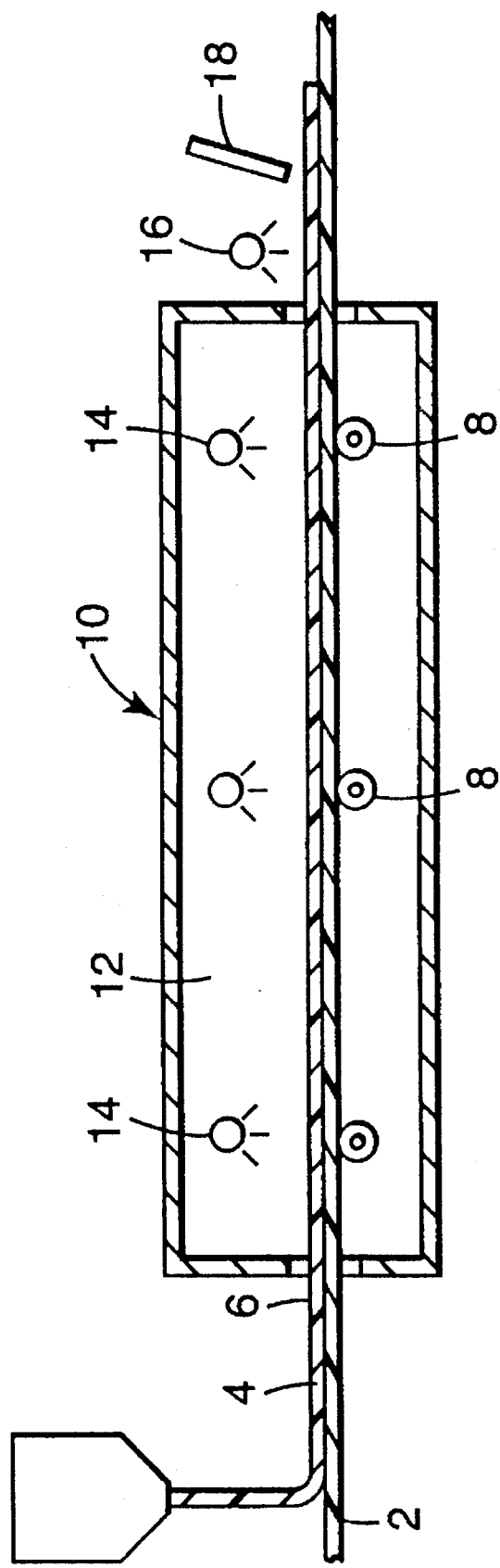
FIG. 1 is a cross section diagram of an example of a coating process utilizing the present invention.

FIG. 1 shows a schematic cross-section of an illustrative example of a process to manufacture coated films, such as coated adhesives. It is to be understood, however, that the methods of the present invention are not limited solely to the processes of coating adhesive film layers, but rather are suitable for use with any other type of radiation-curable system.

Referring to FIG. 1, a substrate 2 is advanced along a path of travel and a radiation-curable coating 4, having an upper major surface 6, is applied thereto. The radiation-curable coating 4 comprises a radiation-curable monomer or oligomer, and a fluorescer, the emission intensity of the fluorescer changing with the concentration of unreacted radiation-curable monomer or oligomer in the coating. The radiation-curable coating 4 and substrate 2 are transported across rollers 8, through cure chamber 10, which encloses an atmosphere 12. Radiant energy sources 14 emit radiant energy onto the radiation-curable coating 4 causing the radiation-curable coating 4 to polymerize or cure; the radiation-cured coating 4 then exits the cure chamber 10.

Radiant energy source 16 emits excitation energy toward the radiation-cured coating 4, on-line, at any time during the cure reaction or after the coating 4 is cured. Detector 18, also at any time during or following the cure process, detects and measures the intensity of the radiation emitted by the fluorescer included in coating 4.

For some coating processes, atmosphere 12 is inert, e.g., the atmosphere comprises nitrogen gas. But, if cure chamber 10 is not air tight, it is possible for oxygen to enter and disperse throughout the inert atmosphere 12 within cure chamber 10. Some of the oxygen can be present at or near the upper surface 6 of coating 4.

The method of applying the radiation-curable coating 4 onto the substrate 2 may be any method known in the art, such as gravure coating, extrusion coating, die coating, knife coating, mayer bar coating, curtain coating, etc.

The substrate 2 used in the practice of the present invention can be of any type known in the art. Preferred substrates include, but are not limited to bi-axially oriented polypropylene (BOPP), polyester, polycoated paper, synthetic paper, polyethylene terephthalate (PET), polyethylene naphthalate, polyethylene, and PET/polyethylene blends.

In the practice of the present invention, the radiation-curable coating 4 comprises a fluorescer, and at least one of a radiation-curable monomer or a radiation-curable oligomer. As used herein, where the term "monomer" is used, it also contemplates the use of an oligomer, which is defined as a polymer unit consisting of only a few monomer units (dimer, trimer, tetramer).

Useful radiation-curable monomers and oligomers are those that will cure, i.e., polymerize (the term polymerize also contemplates a copolymerization reaction), upon being exposed to suitable radiation, with other radiation-curable monomers and/or oligomers, and optionally with a crosslinker, and optionally in the presence of a photo initiator. Examples of useful radiation-curable monomers and oligomers include, but are not limited to epoxies, silanes (SiO—R, wherein R is a reactive group), and ethylenically unsaturated monomers or oligomers.

Examples of generally useful radiation-curable monomers suitable for the practice of the present invention include (meth)acrylate-functional monomers having the general formulas:

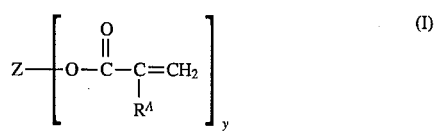

(I)

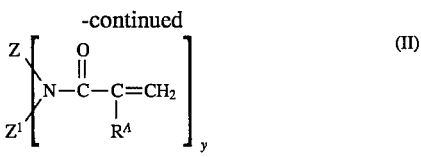

wherein $R^A$ is hydrogen or $CH_3$, and y is preferably in the range from about 1 to 6 (most preferably y is 1). Representative Z groups include those that comprise, for example, hydrogen, amines, silicones, urethanes, polyurethanes, esters, polyesters, oxyalkylene groups, epoxies, alkyl groups, aryl-containing groups, and allyl-containing groups, etc., any of which can be straight, branched, cyclic, aromatic, saturated, or unsaturated. In formula II, the $Z^1$ group can be any of the listed Z groups, and is independent of the identity of the Z group. In the practice of the present invention, monomers of formulas I or II may be polymerized to produce useful oligomers.

The radiation-curable monomers or oligomers preferred in the practice of the present invention comprise an acrylate group; that is, $R^A$ in formula I is hydrogen. Preferred radiation-curable acrylate monomers and oligomers according to formula I include acrylic acid (AA), isooctyl acrylate (IOA), oligomers of IOA, oligomers of AA, and mixtures thereof. Preferred radiation-curable acrylate monomers and oligomers according to formula II include N,N-dimethylacrylamide and oligomers thereof.

Figure 2:
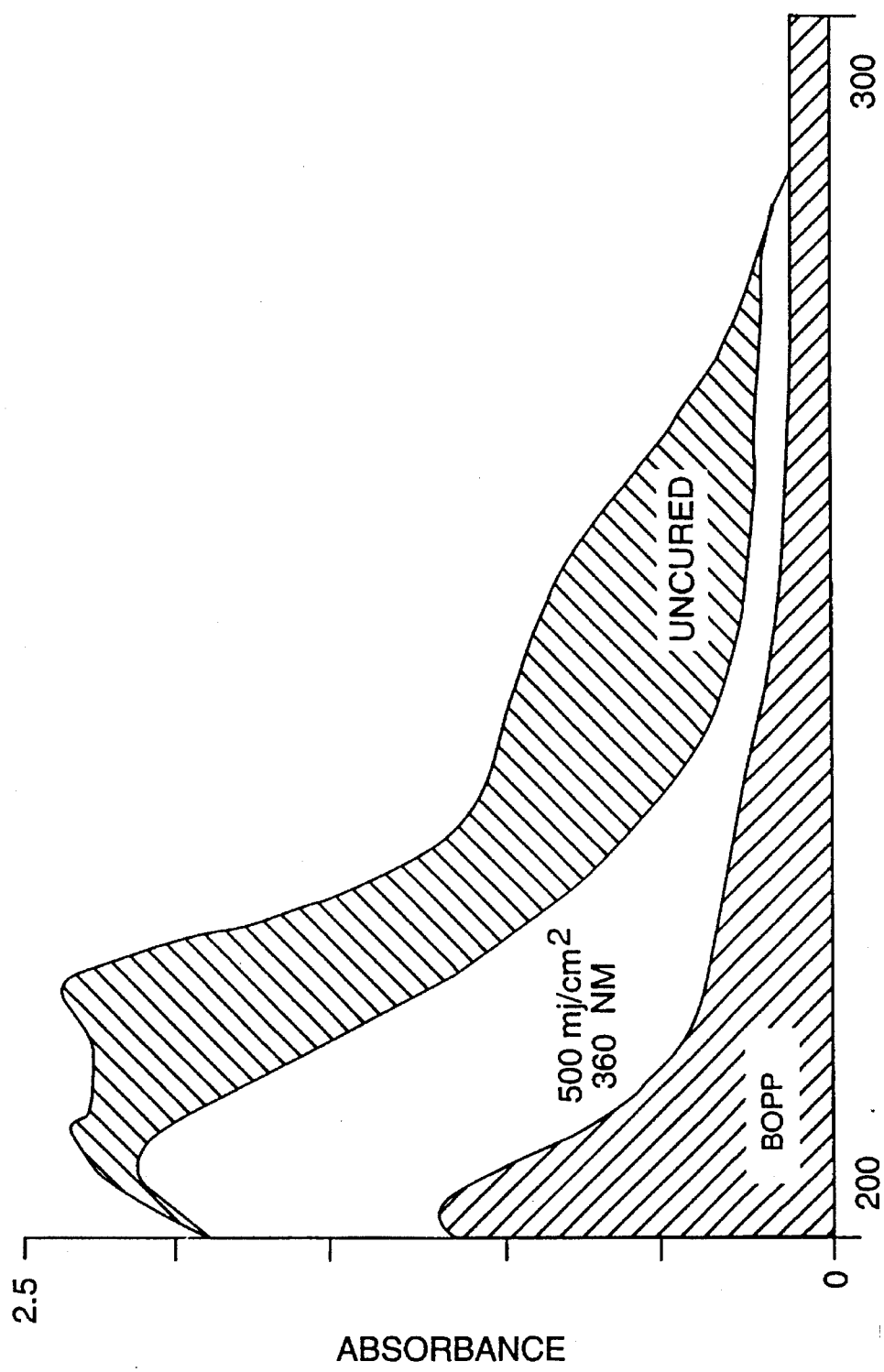
FIG. 2 is a graph depicting the absorbance of a 90:10 (by weight) mixture of IOA:AA monomers at various wavelengths.

Preferably, the radiation-curable monomer or oligomer used in the practice of the present invention absorbs radiant energy of a wavelength range including a wavelength $\lambda_1$, $\lambda_1$ being less than about 300 nm; and, the cured product of the radiation-curable monomer or oligomer absorbs less radiant energy in the same range of wavelengths, including $\lambda_1$, than does the radiation-curable monomer or oligomer. For example, see FIG. 2 showing the absorbance behavior of a 90:10 blend of IOA:AA before and after curing. Most preferably $\lambda_1$ is between the wavelengths of 200 and 300 nm (nanometers), and the monomer or oligomer will strongly absorb radiant energy of a wavelength range that is somewhere between about 200 to 300 nm (e.g., from 205 to 250 nm), while the cured product will absorb less radiant energy in the same range of wavelengths.

In the practice of the present invention, the fluorescer can be any compound which absorbs radiant (excitation) energy of a wavelength $\lambda_2$, and fluoresces radiant energy of a wavelength $\lambda_3$. Typically, the wavelength $\lambda_3$ is included within a range of wavelengths emitted or fluoresced by the fluorescer upon excitation. Also, the excitation wavelength $\lambda_2$ is typically among a range of excitation wavelengths, wherein any wavelength within the range of excitation wavelengths is useful to excite the fluorescer to fluoresce radiant energy over the range of wavelengths including $\lambda_3$. See FIG. 3. Preferably, the range of excitation wavelengths falls somewhere in the range from about 200 to 300 nm. Most preferably, the range of excitation wavelengths overlaps the range of wavelengths wherein the radiation-curable monomer or oligomer absorbs more radiant energy than does the cured product of the radiation-curable monomer or oligomer.

The fluorescence behavior (i.e., emission intensity) of preferred fluorescers changes with the concentration of unreacted radiation-curable monomer or oligomer in the radiation-cured coating. While wishing not to be bound by theory, this can occur through a number of mechanisms. As an example, the range of the excitation wavelengths of the fluorescer preferably overlaps the range at which the radiation-curable monomer or oligomer absorbs radiant energy. Consequently, the presence of unreacted radiation-curable monomer or oligomer reduces the amount of light absorbed by the fluorescer in the overlapping range of wavelengths, and therefore reduces the intensity of fluorescence emission by the fluorescer. This phenomena is known as "competitive absorption."

Alternatively, unreacted radiation-curable monomer or oligomer may cause an excited fluorescer to dissipate its absorbed energy by a mechanism other than fluorescence, thus reducing the emission intensity of the fluorescer. This phenomena is known as "quenching."

Regardless of the mechanism, the intensity of radiant energy fluoresced by a given amount of fluorescer, in the presence of uncured radiation-curable monomers or oligomers, will differ from the intensity of radiant energy fluoresced by the same amount of fluorescer absent the radiation-curable monomer or oligomer; i.e., in the presence of the cured product of the radiation-curable monomer or oligomer. As the curing reaction proceeds and the amount of radiation-curable monomer and/or oligomer in the radiation-curable coating decreases, and the amount of cured product increases, the intensity of radiant energy that would be fluoresced by the fluorescer if exposed to wavelength $\lambda_2$ will change. See FIG. 4. Measuring the emission intensity of the fluorescer in the radiation-cured coating therefore allows a determination of the amount of residual (uncured) radiation-curable monomer or oligomer present in the radiation-cured coating.

As described above, the intensity of radiant energy fluoresced by a fluorescer may decrease due to quenching or competitive absorption of the unreacted monomer or oligomer. Alternatively, the intensity of radiant energy fluoresced by the fluorescer may decreased by the same mechanisms due to the cured product of the radiation-curable monomer or oligomer. In other words, it is possible for the cured product of the radiation-curable monomer or oligomer to absorb radiant energy in competition with the fluorescer, or to quench fluorescence, to a greater degree than the unreacted monomer or oligomer. Thus, the emission intensity of the fluorescer can change either by increasing or by decreasing as the radiation-curable coating cures.

Preferred fluorescers include, but are not limited to biphenyl (commercially available from Aldrich Chemical Co.), fluorene (commercially available from Aldrich), and fluorene derivatives such as n-decyl fluorene, 9,9-dibutyl fluorene, and 9-decyl, 9-methyl fluorene. Of these, biphenyl is most preferred because fluorene and some of the fluorene derivatives tend to cause chain termination during the polymerization reaction of the radiation-curable monomers or oligomers.

The fluorescer can be present in any amount sufficient to absorb excitation energy and emit a spectroscoptically detectable amount of radiant energy. The fluorescer is preferably present in an amount that is sufficiently low so that there is very little radiation absorption by the fluorescer in an uncured coating composition. Generally, for coatings of greater than 1 mil thickness, useful amounts of fluorescer are in the range from about 0.01 to 0.5 pbw (parts by weight) based on 100 parts by weight of radiation-cured coating, with amounts in the range from about 0.02 to 0.2 pbw being preferred. For relatively thinner coatings, i.e. less than about 1 mil, it is often necessary to use a higher concentration of fluorescer to achieve a detectable amount, i.e. up to about 1 pbw based on 100 parts by weight of radiation-cured coating.

Figure 3:
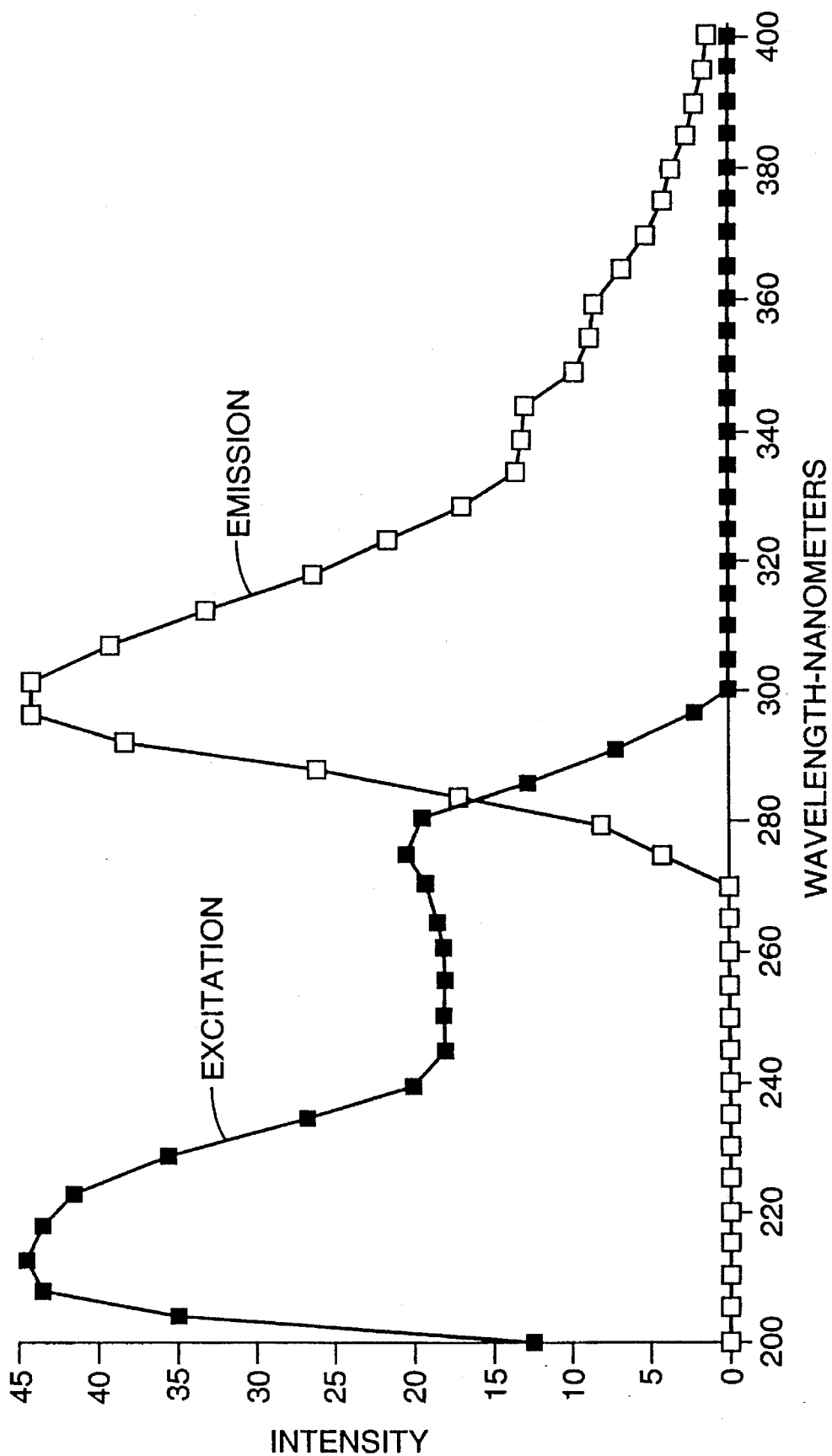
FIG. 3 is a graph illustrating the excitation spectra and the emission spectra of a pure biphenyl fluorescer.

In the practice of the present invention, the intensity of radiant energy fluoresced by a fluorescer can be measured at any wavelength $\lambda_3$ within the range of wavelengths fluoresced by the fluorescer upon excitation. See FIG. 3, showing the excitation behavior and emission behavior of biphenyl fluorescer. Further, any wavelength $\lambda_2$ of the excitation spectra (for biphenyl, from about 200 to 300 nm) can be used to excite the fluorescer and cause fluorescence throughout the range of wavelengths of the emission spectra. Preferably, the excitation wavelength $\lambda_2$ is chosen to prevent interference with the measured emission wavelength $\lambda_3$. For example with a biphenyl fluorescer, the excitation energy used to measure fluorescence emission at a wavelength of about 290 nm is preferably less than about 270 nm.

Measurements of the intensity of radiant energy fluoresced by the fluorescer are preferably taken either on-line (during cure), or immediately thereafter. If a significant period of time passes between cure and measuring emission intensity, it is possible for residual monomer or oligomer to evaporate, thereby causing the fluorescence intensity to change.

Measurement of the intensity of radiant energy fluoresced by the fluorescer is limited to the depth that excitation energy penetrates the radiation-cured coating. Only the fluorescer that absorbs and is excited by the excitation energy will fluoresce. The penetration of the excitation energy into the radiation-cured coating in turn depends on the chosen wavelength of excitation energy. Excitation energy of relatively shorter wavelengths will penetrate less of the radiation-cured coating than will excitation energy of relatively longer wavelengths. Therefore, the depth to which a fluorescer, and therefore residual monomer or oligomer, is detected depends on the wavelength of the excitation energy used.

The use of excitation energy having a relatively shorter wavelength provides a means of detecting fluorescer, and therefore residual monomer or oligomer, in an upper portion (near the upper major surface) of a radiation-cured coating. This is particularly important when curing (meth)acrylate-containing coatings, wherein polymerization is most often retarded at or near the coating surface. In the practice of the present invention, it is preferred that at least 50% of the excitation energy is absorbed by the upper 75 µm of the radiation-cured coating. To accomplish this result, the wavelength $\lambda_2$ of the excitation energy is preferably in the range from about 200 to 300 nm.

The present method, by detecting fluorescer, and radiation-curable monomer or oligomer, located at or near the upper surface of the radiation-cured coating, allows very high sensitivity in determining the amount of residual radiation-curable monomer or oligomer present in a radiation-cured coating. Specifically, the method of the present invention can be used to determine the amount of residual radiation-curable monomer or oligomer present in a radiation-cured coating at cure levels up to and exceeding 90% cure, i.e. this method is sensitive enough to detect 10% or less by weight of residual monomer or oligomer; and even less than 2% or 1% by weight residual monomer or oligomer in a radiation-cured coating.

Measuring the emission intensity of a fluorescer can also lead to other information useful in producing radiation-cured materials. For example, residual monomer or oligomer content can be correlated to physical properties. Knowing the amount of residual monomer or oligomer in a coating, especially at the coating's surface, can allow the prediction of various performance characteristics of a radiation-cured product. The particular characteristic will depend on the application of the coating, but as an example, adhesion and tack properties can be predicted for adhesive coatings. Other properties can be predicted for other applications, including abrasion resistance, odor, release properties, and cosmetic properties such as gloss. As another example, the present invention provides a means to determine the amount of oxygen present in a cure chamber at the time a radiation-cured coating is cured.

The polymerization of many radiation-curable coatings can be inhibited by oxygen. In such cases, it is desirable to cure the radiation-curable coating in an atmosphere that has been purged of oxygen, e.g., in a nitrogen-purged cure chamber. For many reasons, oxygen may be present even in a purged cure chamber. For example the purge process can be imperfect, or, oxygen might enter the cure chamber during the curing process. This oxygen might reach the surface of the coating in the cure chamber and potentially inhibit the cure of the surface of the coating, causing one or more of the following: an increased concentration of residual monomer at the coating's surface, an increased concentration of oxygen at the coating's surface, a lower average molecular weight cure product.

Figure 5:
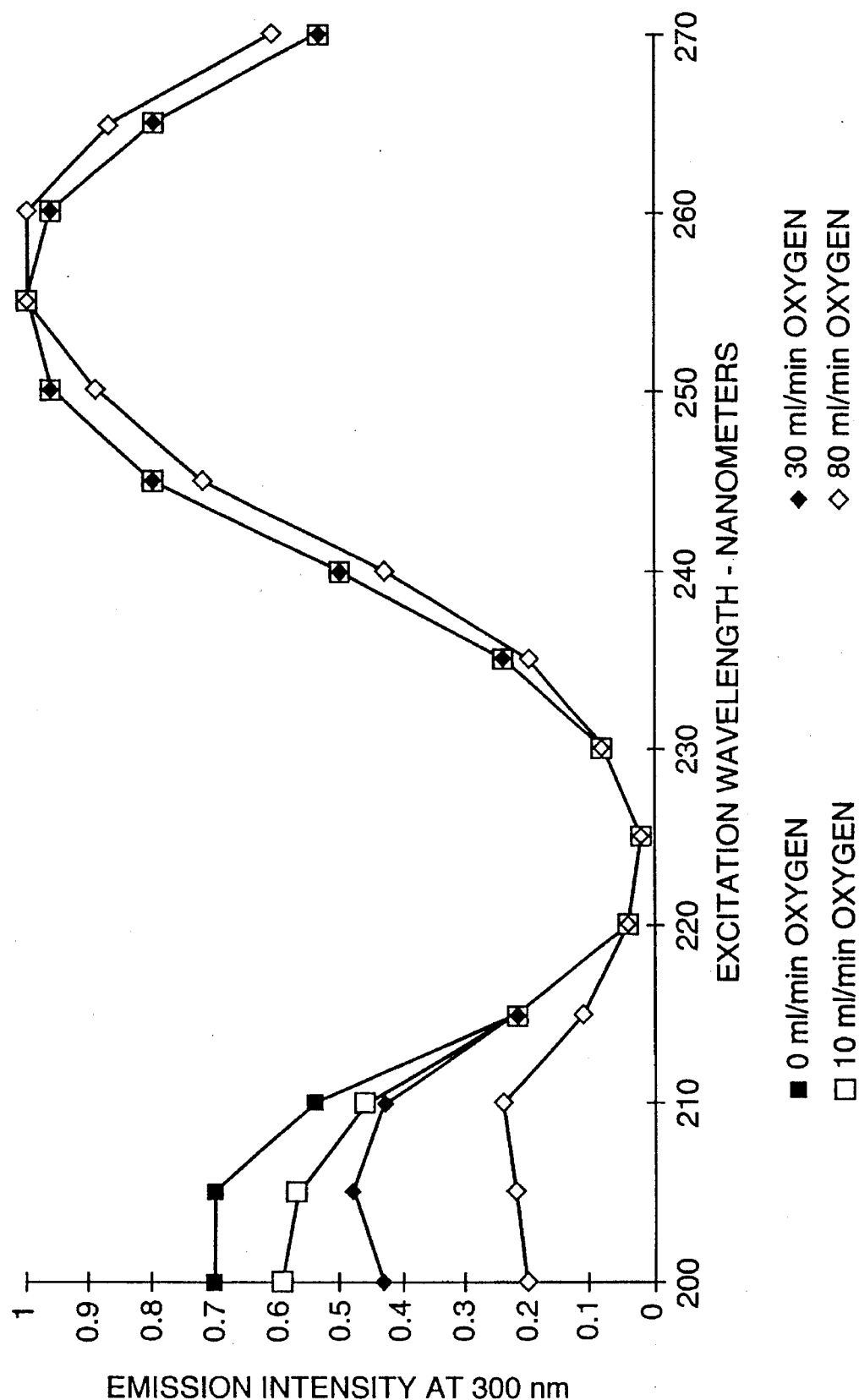
FIG. 5 is a graph depicting the effects of oxygen on the normalized fluorescence emission intensity of a composition comprising 90:10 (by weight) IOA:AA and 0.02% by weight biphenyl fluorescer, as measured at various wavelengths.

It has been discovered that the intensity of the radiant energy fluoresced by a fluorescer within a radiation-cured coating may change with the concentration of oxygen in the cure chamber at the time the coating is cured. This is evidenced in FIG. 5. FIG. 5 illustrates that the normalized emission intensity of a fluorescer excited by energy of the range of wavelengths from about 200 to 220 nm decreases as the amount of oxygen in the cure chamber increases. This relationship provides a means to determine, by reference to predetermined calibration data, the amount of oxygen present in a purged cure chamber. Predetermined calibration data can be any data relating the emission intensity of a fluorescer to the oxygen content of a purged cure chamber; an example is FIG. 5.

When using the present method to determine the oxygen content of a cure chamber, the penetration of the excitation energy into the radiation-cured coating depends on the wavelength of the excitation energy. Relatively longer wavelength radiant energy will penetrate further into the radiation-cured coating. In the practice of the present invention, it is preferred that at least 50% of the excitation energy is absorbed by the upper 75 µm of the radiation-cured coating. To accomplish this result, the wavelength $\lambda_2$ of the excitation energy is preferably in the range from about 200 to 215 nm, with the range from about 200 to 205 nm being most preferred. By using excitation energy in this range, the present method detects the effects of oxygen in a cure chamber as they occur at or near the upper surface of the radiation-cured coating.

In the practice of the present invention, the radiation-curable coating may further comprise other ingredients known to be useful in the production of radiation-curable coatings. For example, the radiation-curable coating may comprise any crosslinker known in the art to be useful in curing radiation-curable monomers or oligomers. An appropriate crosslinker can be chosen based upon the choice of radiation-curable monomer or oligomer. When the radiation-curable monomer comprises an acrylate group, an example of a preferred crosslinker is a multi-functional acrylate. Other preferred crosslinkers include triallyl cyanurate, and triazines such as 2,4-bis(trichloromethyl)-6-(4-methoxyphenyl)-s-triazine. Triazines can be prepared by the co-trimerization of an aryl nitrile with trichloroacetonitrile in the presence of HCl gas and a Lewis acid such as $AlCl_3$, $AlBr_3$, etc. (see Bull. Chem. Soc. Japan, Vol. 42 page 2924 (1969)).

Optionally, the radiation-curable coating may further comprise a photo initiator. The photo initiator can be chosen to work with the radiation-curable monomer and optional crosslinker to provide a radiation-curable coating that will polymerize upon exposure to appropriate radiant energy. Photo initiators useful with various radiation-curable monomers or oligomers are known in the art.

In the practice of the present invention radiant energy source 14 is used in curing the radiation-curable coating. Radiant energy source 14 may be any type of radiant energy source that will cause polymerization of the radiation-curable monomers or oligomers alone, or in the presence of an optional crosslinker or photo initiator. Examples of useful radiant energy sources include those that emit thermal energy (heat or infra-red radiation), e-beam radiation, microwave radiation, UV radiation, γ-radiation, visible radiation, and the like. The wavelength of light emitted by the radiant energy source can be chosen to correspond to the composition of the radiation-curable coating, i.e., the radiation-curable monomer or oligomer, and any crosslinker or photo initiator. The curing wavelength may also be chosen to effect curing preferences. For example, a shorter wavelength may be used to effect a relatively higher level of cure at the surface of a radiation-curable coating. Preferably, the radiant energy emitted by the radiant energy source 14 is in the range from about 280 to 400 nm. Examples of suitable radiant energy sources include, but are not limited to, low pressure mercury bulbs, medium pressure mercury bulbs, and fluorescent black light bulbs.

In the practice of the present invention, the radiant energy source 16 that emits excitation energy onto the coating may be any type of radiant energy source that will cause excitation of the fluorescer. The wavelength of the light emitted by the radiant energy source can be chosen to correspond to the excitation energy of the fluorescer, i.e., the fluorescer will absorb excitation energy from the radiant energy source 16, and emit radiant energy of wavelength $\lambda_3$. Preferably, the radiant energy emitted by the radiant energy source 16 is in the range from about 200 to 300 nm. Examples of suitable radiant energy sources include, but are not limited to xenon bulbs.

In the practice of the present invention the detector 18 can be any type of detector capable of detecting and measuring the intensity of radiant energy emitted by the fluorescer. An example of a suitable detector is a photomultiplier tube and apparatus, of types known in the art.

Preferably, in the practice of the present invention, a single Fluorescence Spectrophotometer, such as the Perkin Elmer MPF-66, can be used to introduce excitation energy to a sample and also to collect and measure the intensity of fluorescence emission.

The method of the present invention allows for on-line measurement of the precise amount of residual radiation-curable monomer or oligomer present in a radiation-cured material. The measurement can be used for feedback control of various process parameters. For instance, by determining the precise level of cure of a radiation-cured coating, process parameters, including but not limited to line speed, intensity of cure lights, flow rates of an inert purge gas (e.g., nitrogen), etc., can be immediately adjusted to increase or decrease the level of cure of the cured product.

Alternatively, the information obtained by the method of the present invention may be used to design improved cure systems. For instance, determining how much oxygen is present in a purged cure chamber is useful for designing a cure chamber that will allow less oxygen to enter the cure chamber, or interfering with cure at the coating's surface. Other process parameters, for example the intensity of cure exposure, could be the subject of similar optimization studies.

The objects and advantages of the present invention are further illustrated by the following non-limiting examples. The particular materials, conditions and details recited in these examples should not be construed to unduly limit this invention.

EXAMPLE 1

Because the compositions of radiation-curable coatings useful with the method of the present invention are various, an exemplary radiation-curable system was chosen to demonstrate the present invention of measuring residual monomers. The present example included a radiation-curable adhesive (hereinafter referred to as Coating 1) comprising 90 parts by weight isooctyl acrylate monomer (IOA), 10 pbw acrylic acid monomer (AA), and 0.02% by weight biphenyl fluorescer.

A 1 mil (25 μm) layer sample of Coating 1 was "sandwiched" between two layers of biaxially oriented polypropylene (BOPP). One sample remained uncured, and another sample was cured with 500 mj/cm$^2$ of 360 nm light. The absorption spectra of the cured and uncured samples were measured using a Hewlett Packard Absorption UV-Vis Spectrophotometer. FIG. 2 shows the UV absorption spectra of the uncured and cured samples of Coating 1, as well as the absorption of the BOPP substrate. FIG. 2 indicates that the absorbance behavior of the IOA/AA composition of Coating 1 decreased significantly when exposed to ultraviolet radiation. More specifically, the amount of radiant energy absorbed by Coating 1 throughout the wavelength range between about 200 and 280 nm, and especially the range between about 210 and 260 nm, decreased substantially with exposure to radiant energy of a wavelength of 360 nm. The reason for this dramatic decrease in absorption between the radiation-curable coating and the radiation-cured coating was the disappearance of the radiation-curable monomers of IOA and AA due to their polymerization upon cure.

FIG. 3 shows the fluorescence characteristics of pure biphenyl. Biphenyl, could be excited at wavelengths in the range from about 200 to 300 nm, and especially at wavelengths in the range from about 200 to 270 nm. FIG. 3 shows that upon excitation, the biphenyl fluorescer would fluoresce radiant energy of the wavelength range from about 280 to 380 nm, with especially strong fluorescence in the range from about 290 to 340 nm.

Figure 4:
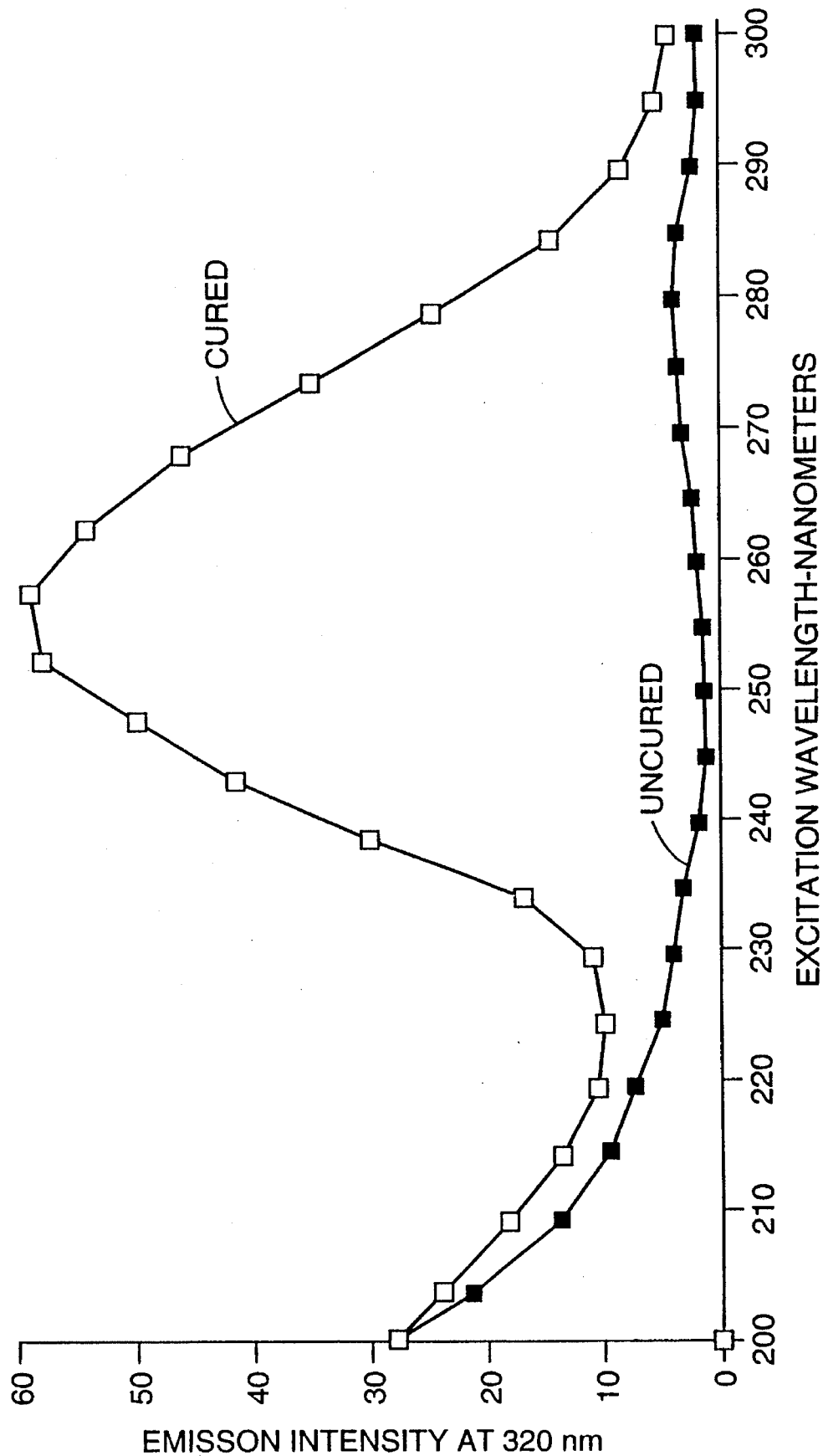
FIG. 4 is a graph illustrating, throughout a range wavelengths, the emission intensity of 0.02% by weight biphenyl fluorescer included in a 90:10 (by weight) mixture of IOA:AA monomers, both before and after the composition has been cured.

The fluorescence emission intensity of Coating 1 was measured before and after cure, to observe a change in the emission intensity of the fluorescer upon cure. FIG. 4 graphs intensity of the fluorescence emission of Coating 1, measured at 320 nm, caused by a range of excitation energies. The "uncured" curve indicates the emission intensity of an uncured sample, and the "cured" curve indicates the emission intensity of the sample after being cured by 300 mj/cm$^2$ radiant energy of about 350 nm.

According to FIG. 4, the biphenyl fluorescer in the uncured sample of Coating 1 was not excited by energy of the wavelength range between about 220 to 300 nm. The fluorescer in the uncured sample was, however, excited by energy of wavelengths from about 200 to 220 nm. The biphenyl fluorescer in the cured sample of Coating 1 was excited to fluoresce by excitation energy throughout the entire wavelength range from about 200 to 300 nm, and especially by the wavelength ranges from about 200 to 215 nm, and 235 to 285 nm.

FIG. 4 illustrates that the emission intensity of the biphenyl fluorescer at 320 nm, as caused by excitation wavelengths including the range from about 235 to 285, increased significantly after the sample of Coating 1 was cured. The change in fluorescence was due to the decreased amount of radiation-curable IOA and AA monomer present in the sample of Coating 1. By measuring the intensity of the fluorescence emission of the fluorescer at 320 nm, as produced by excitation energy of a wavelength within the range from about 235 to 285, the amount of residual monomer in the radiation-cured coating could be determined.

FIG. 4 indicates that a broad range of excitation wavelengths ($\lambda_2$) could be used to excite the biphenyl fluorescer, and thereby measure a change in residual monomer content of the radiation-cured coating. The greatest sensitivity with this particular system would be attained by using a wavelength of about 257 nm.

EXAMPLE 2

Seven samples of a radiation-curable composition were produced containing 90 parts by weight IOA, 10 parts by weight AA, 0.15% of ESCACURE KB-1 photo initiator available from Sartomer, 0.1% of n-decyl fluorene fluorescer, and 0.1% of 2,4-bis(trichloromethyl)-6-(4-methoxyphenyl)-s-triazine. The samples were cured by exposure to various amounts of 350 nm UV energy, of intensities ranging from 192–500 mj/cm$^2$, to produce a set of samples of various levels of cure.

The present example provides a correlation between the change in the residual monomer concentration of the radiation-cured coating, and the change observed in the samples' fluorescence emission intensity. The procedure involved redry testing to quantify the amount of residual monomer in each sample, and also, measuring fluorescence before and after the redry testing.

First, each sample was weighed. Next, using a Perkin Elmer MPF-66 Fluorescence Spectrophotometer, the fluorescence intensity of each sample at 320 nm was measured while being excited by 254 nm light. Each sample was heated on a 150° F. (65° C.) hot plate for 5 minutes in order to evaporate off any residual monomer. The mass of the redried sample was then taken, and the sample's fluorescence emission at 320 nm was again measured by illuminating the sample with 254 nm light. The results are given in Table 1.

Table 1 illustrates the high sensitivity of the present method of determining residual monomer content. On average, a 4.44% change in the concentration of radiation-curable monomer, as determined by redry testing, correlated to approximately a 29.7% change in emission intensity of the fluorescer by the present method. In other words, a 1% change in radiation-curable monomer can be detected as approximately a 7% change in the emission intensity of the fluorescer.

EXAMPLE 3

A radiation-curable composition was produced comprising 90 pbw of IOA, and 10 pbw AA, 0.1 wt % 1,6-hexanediol diacrylate crosslinker (commercially available from Sartomer), and 0.02% by weight biphenyl. The radiation-cured coating was applied to a substrate and cured in a cure chamber purged with a constant flow of nitrogen gas. To generate calibration data correlating the effect of oxygen in the purge chamber to the emission intensity of the fluorescer, the nitrogen purge gas also contained various concentrations of oxygen, as indicated in FIG. 5.

The samples were cured individually in the cure chamber under identical cure conditions except for the different concentration of oxygen in the purge gases. Using a Perkin Elmer MPF-66 Fluorescence Spectrophotometer an excitation scan of each sample was taken between the range of 200 to 270 nm by illuminating the sample with a specific wavelength light, and measuring the emission intensity of the biphenyl fluorescer at a wavelength of 300 nm. FIG. 5 graphs the emission intensity of the fluorescer at 300 nm versus the excitation wavelength used to excite the fluorescer, for samples cured in an atmosphere of nitrogen and various concentrations of oxygen. The graph of FIG. 5 is normalized to remove the random effects of exposure intensity and time of exposure of the samples in the cure chamber.

FIG. 5 illustrates that the emission intensity of the fluorescer caused by an excitation energy of 200 nm changes with the concentration of oxygen in the cure chamber. By measuring the emission intensity (at 300 nm) of the fluorescer in other samples, caused by an excitation wavelength of 200 nm, the amount of oxygen present in the cure chamber used to cure the other samples can be determined by comparison to the calibrated data of FIG. 5.

What is claimed is:

1. A method of measuring intensity of radiant energy fluoresced by a fluorescer in a radiation-cured coating, the method comprising the steps of:

a) providing a coating comprising:

TABLE 1

| | | Before Heating | | After Heating | |
|---|---|---|---|---|---|
| | BOPP weight (gms) | Coated film weight (gms) | Fluorescence intensity of n-decyl fluorene | Coated film weight (gms) | Fluorescence intensity of n-decyl fluorene |
| 1 | 0.0723 | 0.1122 | 69.20 | 0.1101 | 114.0 |
| 2 | 0.0718 | 5.1055 | 59.20 | 0.1061 | 110.0 |
| 3 | 0.0719 | 0.1102 | 75.00 | 0.1095 | 82.0 |
| 4 | 0.0722 | 0.1109 | 58.50 | 0.1097 | 101.0 |
| 5 | 0.0733 | 0.1093 | 75.50 | 0.1082 | 95.0 |
| 6 | 0.0714 | 0.1118 | 74.00 | 0.1103 | 96.4 |
| 7 | 0.0693 | 0.1068 | 80.40 | 0.1042 | 102.0 |
| Avg. | 0.0717 | 0.1100 | 70.3 | 0.1083 | 100.0 |
| Std. Dev. | 0.00123 | 0.00191 | 8.45 | 0.00232 | 10.51 |

Change in monomer concentration as measured by redry = (0.1100–0.0717) – (0.1083–0.0717)/(0.1100–0.0717)
= 4.44%
Change in Fluorescence = (100 – 70.3)/100.0 = 29.70% i) a radiation-curable monomer or oligomer; and ii) a fluorescer having an excitation energy at a wavelength $\lambda_2$, the fluorescer fluorescing radiant energy of a wavelength $\lambda_3$;

b) curing the coating by exposure to radiant energy, thereby changing the intensity of radiant energy that would be fluoresced by the fluorescer if exposed to wavelength $\lambda_2$;

c) illuminating the radiation-cured coating with excitation energy of a wavelength $\lambda_2$, wherein at least 50% of the excitation energy is absorbed by the upper 75 μm of the radiation-cured coating; and d) measuring the intensity of the radiant energy fluoresced by the fluorescer at wavelength $\lambda_3$.

2. A method for measuring the amount of residual radiation-curable monomer or oligomer in a radiation-cured coating, the method comprising the steps of:

a) providing a coating comprising:

i) a radiation-curable monomer or oligomer; and ii) a fluorescer having an excitation energy at a wavelength $\lambda_2$, the fluorescer fluorescing radiant energy of a wavelength $\lambda_3$, wherein the intensity of the fluoresced radiant energy of wavelength $\lambda_3$ changes with the concentration of unreacted radiation-curable monomer or oligomer in the coating;

b) curing the coating by exposure to radiant energy;

c) illuminating the radiation-cured coating with excitation energy of a wavelength $\lambda_2$, wherein at least 50% of the excitation energy is absorbed by the upper 75 μm of the radiation-cured coating; and d) measuring the intensity of the radiant energy fluoresced by the fluorescer at wavelength $\lambda_3$;

e) from the intensity measurement, determining the amount of residual radiation-curable monomer or oligomer present in the radiation-cured coating.

3. The method of claim 2, wherein the method is used to measure radiation curable monomer at levels of cure equal to or greater than 90%.

4. The method of claim 2, wherein the radiation-curable monomer or oligomer absorbs radiant energy of a wavelength $\lambda_1$, $\lambda_1$ being less than 300 nm, and the cured product of the radiation-curable monomer or oligomer absorbs less radiant energy at wavelength $\lambda_1$ than does the radiation-curable monomer or oligomer.

5. The method of claim 4, wherein the radiation-curable monomer comprises a (meth)acrylate group.

6. The method of claim 5, wherein the radiation-curable monomer is chosen from the group consisting of isooctyl acrylate, acrylic acid, N,N-dimethylacrylamide, and mixtures thereof.

7. The method of claim 6, wherein the radiation-curable monomer is isooctyl acrylate.

8. The method of claim 6, wherein the radiation-curable monomer is acrylic acid.

9. The method of claim 6, wherein the radiation-curable monomer is a mixture of isooctyl acrylate and acrylic acid.

10. The method of claim 9, wherein $\lambda_1$ is in the range between about 210 and 260 nm.

11. The method of claim 2, wherein the fluorescer is chosen from the group consisting of biphenyl, fluorene, n-decyl fluorene, 9,9-dibutyl fluorene, and 9-decyl, 9-methyl fluorene.

12. The method of claim 11, wherein the fluorescer is biphenyl.

13. The method of claim 12, wherein $\lambda_2$ is in the range from about 200 to 300 nm.

14. The method of claim 13, wherein $\lambda_2$ is in the range from about 235 to 285 nm.

15. The method of claim 14, wherein $\lambda_2$ is about 257 nm.

16. The method of claim 12, wherein $\lambda_3$ is in the range from about 290 to 340 nm.

17. A method of measuring the concentration of oxygen in a cure chamber, the method comprising the steps of:

a) providing a coating in a cure chamber, the coating comprising:

i) a radiation-curable monomer or oligomer; and ii) a fluorescer having an excitation energy at a wavelength $\lambda_2$, the fluorescer fluorescing radiant energy of a wavelength $\lambda_3$, wherein the intensity of the fluoresced radiant energy at wavelength $\lambda_3$ changes with the concentration of oxygen in the cure chamber at the time the coating is cured;

b) curing the coating by exposure to radiant energy;

c) illuminating the radiation-cured coating with excitation energy of a wavelength $\lambda_2$;

d) measuring the intensity of the radiant energy fluoresced by the fluorescer at wavelength $\lambda_3$; and e) relating the intensity of the radiant energy fluoresced by the fluorescer at $\lambda_3$ to the concentration of oxygen present in the cure chamber at the time the coating is cured by reference to predetermined calibration data.

18. The method of claim 17, wherein the coating comprises an upper major surface and at least 50% of the excitation energy is absorbed by the upper 75 μm of the radiation-cured coating.

19. The method of claim 17, wherein the radiation-curable monomer comprises a (meth)acrylate group.

20. The method of claim 19, wherein the radiation-curable monomer is chosen from the group consisting of isooctyl acrylate, acrylic acid, N,N-dimethylacrylamide, and mixtures thereof.

21. The method of claim 20, wherein the radiation-curable monomer is isooctyl acrylate.

22. The method of claim 20, wherein the radiation-curable monomer is acrylic acid.

23. The method of claim 20, wherein the radiation-curable monomer is a mixture of isooctyl acrylate and acrylic acid.

24. The method of claim 17, wherein the fluorescer is chosen from the group consisting of biphenyl, fluorene, n-decyl fluorene, 9,9-dibutyl fluorene, and 9-decyl, 9-methyl fluorene.

25. The method of claim 24, wherein the fluorescer is biphenyl.

26. The method of claim 25, wherein $\lambda_2$ is in the range from about 200 to 215 nm.

27. The method of claim 25, wherein $\lambda_3$ is in the range from about 290 to 340 nm.

* * * * *